United States Patent [19]

Weiss et al.

[11] Patent Number: 4,847,419

[45] Date of Patent: * Jul. 11, 1989

[54] PROCESS FOR THE PREPARATION OF BIFUNCTIONAL TERTIARY AROMATIC PHOSPHINE SULFIDES, AND ALSO SEVERAL SPECIFIC REPRESENTATIVES OF THIS CLASS OF COMPOUNDS

[75] Inventors: Erwin Weiss, Hofheim am Taunus; Hans-Jerg Kleiner, Kronberg/Taunus, both of Fed. Rep. of Germany

[73] Assignee: Hoechst Aktiengesell, Frankfurt am Main, Fed. Rep. of Germany

[ * ] Notice: The portion of the term of this patent subsequent to Jun. 2, 2004 has been disclaimed.

[21] Appl. No.: 4,167

[22] Filed: Jan. 15, 1987

Related U.S. Application Data

[63] Continuation-in-part of Ser. No. 756,326, Jul. 10, 1985, Pat. No. 4,670,601.

[30] Foreign Application Priority Data

Jan. 17, 1986 [DE] Fed. Rep. of Germany ....... 3601247

[51] Int. Cl.$^4$ .............................................. C07F 9/02
[52] U.S. Cl. ...................................................... 568/14
[58] Field of Search .......................................... 568/14

[56] References Cited

U.S. PATENT DOCUMENTS 4,670,601  6/1987  Kleiner et al. ....................... 568/14

*Primary Examiner*—Paul F. Shaver
*Attorney, Agent, or Firm*—Connolly & Hutz

[57] ABSTRACT

A compound of the formula I,

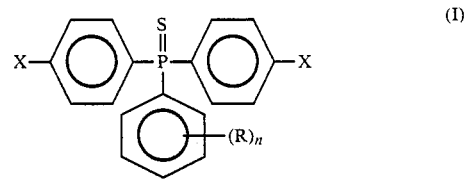

in which
X is F, Cl or Br,
R is alkyl having from 1 to 5 carbon atoms, aryl, aryloxy or aralkyl and
n is an integer from 1 to 5, a plurality of R representing equal or different of said substituents and a process for preparing them.

18 Claims, No Drawings

PROCESS FOR THE PREPARATION OF BIFUNCTIONAL TERTIARY AROMATIC PHOSPHINE SULFIDES, AND ALSO SEVERAL SPECIFIC REPRESENTATIVES OF THIS CLASS OF COMPOUNDS

This application is a continuation-in-part of U.S. application Ser. No. 756,326 filed July 10, 1985 by Erwin Weiss and Hans-Jerg Kleiner, now U.S. Pat. No. 4,670,601.

Bifunctional tertiary aromatic phosphine sulfides are, inter alia, the bis(4-halophenyl)phenylphosphine sulfides of the formula

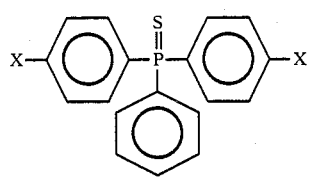

in which X=halogen.

They are valuable final products and intermediates in various fields.

Final products are bis(4-halophenyl)phenylphosphine sulfides (and oxides), which may be used, for example, in the plant protection sector as insecticides and acaricides (German Offenlegungsschrift No. 2,743,848=U.S. Pat. No. 4,101,655).

Intermediates are the compounds, for example, in the polymers sector. For use in this area, the compounds must first be converted (by an oxidative route) into the corresponding phosphine oxides, which can then be condensed with certain bisphenols to form valuable polymers (German Offenlegungsschrift No. 3,203,186), for example:

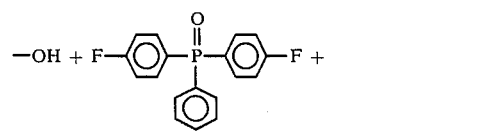

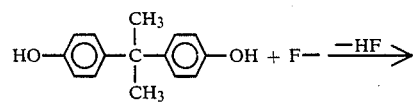

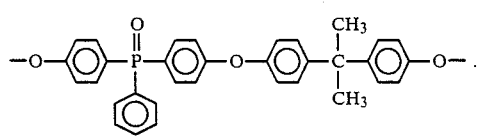

The polymers are distinguished by particular non-flammability and extreme thermal stability; they can be processed into fibers, films and molded articles, etc.

The bis(4-halophenyl)phenylphosphine sulfides may—as indicated in the abovementioned German Offenlegungsschrift No. 2,743,848—be prepared, for example, by Grignard reaction of dichlorophenylphosphine with halophenylmagnesium halide and subsequent reaction with elemental sulfur corresponding to the reaction equations below (schematic):

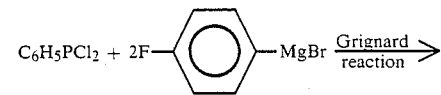

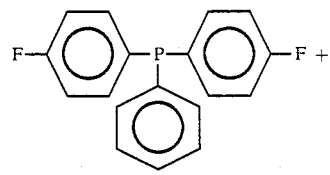

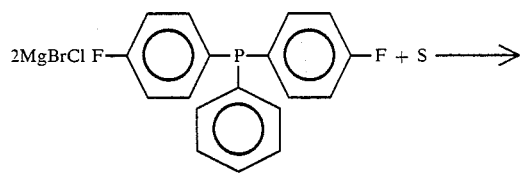

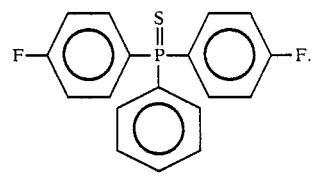

If, in the second reaction step, hydrogen peroxide $H_2O_2$ is employed in place of the elemental sulfur, the corresponding phosphine oxides are obtained directly:

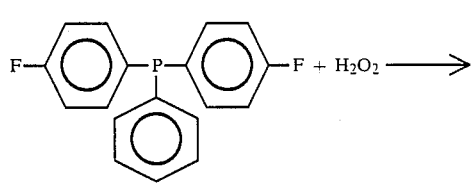

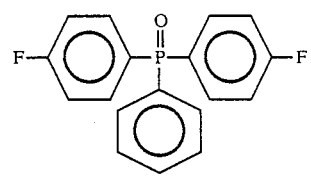

The phosphine oxides may alternatively be obtained by a Grignard reaction of phenylphosphonic dichloride with halophenylmagnesium halide:

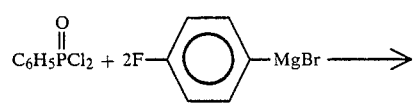

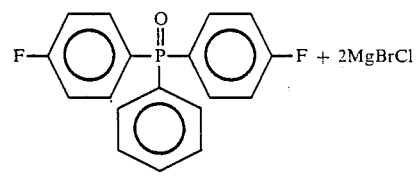

Finally, the preparation of arylated thiophosphorous compounds, such as bis(4-halophenyl)phenylphosphine sulfides, is also possible by the process of German Patent No. 1,238,024 by Friedel-Crafts reaction of thiophosphorus halide compounds such as phenylthiophosphonic dichloride $C_6H_5P(S)Cl_2$, with aromatic compounds, such as halobenzenes, in the presence of an at least equimolar amount, relative to the thiophosphorus halide compound, of a Friedel-Crafts catalyst (particularly $AlCl_3$), and with an at least equimolar amount, relative to the halogen atoms to be replaced, of the aromatic compounds, with subsequent decomposition of the resultant catalyst complex compound using water, ice or, in a fashion which is known per se, by addition of a compound which forms a stronger complex with the catalyst than does the thiophosphorus compound to be isolated. In the case of the preparation, for example, of bis(4-fluorophenyl)phenylphosphine sulfide by this process, the appropriate reaction equation would be:

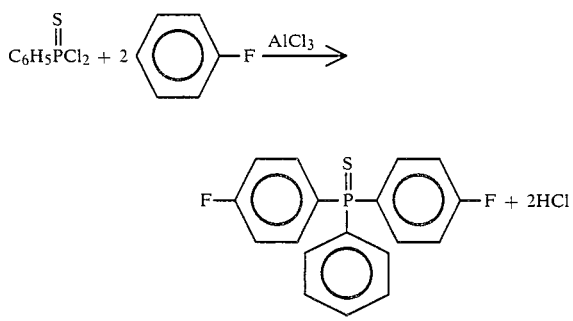

However, the preparation of this compound and also of other bis(4-halophenyl)phenylphosphine sulfides is not supported by examples in the German patent mentioned. The only examples which relate to reaction with a halobenzene are examples 7, 8 and 9 (reaction of $PSCl_3$ with chlorobenzene) and also 15 and 16 (reaction of $PSCl_3$ with fluorobenzene).

According to Example 7, phosphorus thiochloride $PSCl_3$, $AlCl_3$ and chlorobenzene $C_6H_5Cl$ in the molar ratio 1:5.33:6.67 are refluxed for 7 hours. 64%, relative to the $PSCl_3$ employed, is specified as the yield of tris(chlorophenyl)phosphine sulfide; according to the IR spectrum, the product is said to comprise approximately equal parts of the o- and p-isomers.

In Example 8, the $PSCl_3$:$AlCl_3$:$C_6H_5Cl$ molar ratio is 1:2:4. The following is said to have been obtained after refluxing for 1¼ hours:

63.2% of bis(chlorophenyl)thiophosphinic chloride $(C_6H_4Cl)_2P(S)Cl$ (after recrystallization), and also a not insignificant amount of a residue which is said to have comprised a mixture of isomeric tris(chlorophenyl)phosphine sulfides $(C_6H_4Cl)_3PS$.

In Example 9, the $PSCl_3$:$AlCl_3$:$C_6H_5Cl$ ratio was 1:2.5:1. The following are said to have been obtained after refluxing for one hour:

45.4% of chlorophenylthiophosphonic dichloride $(C_6H_4Cl)P(S)Cl_2$, 19.7% of bis(chlorophenyl)thiophosphinic chloride $(C_6H_4Cl)_2P(S)Cl$ as an isomeric mixture, and 18.3% of tris(chlorophenyl)phosphine sulfide $(C_6H_4Cl)_3P(S)$.

Isomeric mixtures are only mentioned in the case of the product of Example 7, the residue of Example 8 and the middle fraction of Example 9. However, it can hardly be imagined that the other chlorophenyl products were then free of isomers to any extent. Corresponding isomeric mixtures can thus certainly be presumed in the case of all reaction products.

According to Example 15, $PSCl_3$, $AlCl_3$ and fluorobenzene $C_6H_5F$ in the molar ratio 1:5.33:6.67 were refluxed for 4 hours. 79.5% of bis(4-fluorophenyl)thiophosphinic chloride $(C_6H_4F)_2P(S)Cl$ which was virtually free of isomers, having only a trace of the o-isomer, and also a small residue are said to have been obtained.

In Example 16, the $PSCl_3$:$AlCl_3$:$C_6H_5F$ molar ratio was 1:2.2:1.1. The result after refluxing for 1¾ hours was:

23.2% of virtually pure fluorophenylthiophosphinic dichloride $(C_6H_4F)P(S)Cl_2$, 14.2% of bis(fluorophenyl)thiophosphinic chloride $(C_6H_4F)_2P(S)Cl$ (without specification of the isomeric purity), and also a not insignificant amount of a brown residue.

In order to obtain the bis(4-halophenyl)phenylphosphine sulfides from the bis(4-halophenyl)thiophosphinic chloride obtained in more or less high yields according to these examples, the bis(4-halophenyl)thiophosphinic chlorides would have to be subjected, after their isolation and, if appropriate, separation of the isomers, to a further Friedel-Craft reaction with benzene.

The phosphine oxides which are necessary for the polymers sector could be obtained from the phosphine sulfides by reaction, for example, with $SOCl_2$ or with oxidants such as $KMnO_4$; cf. for example, the article by L. Maier—also the inventor of the abovementioned German Patent No. 1,238,024— in Helvetica Chimica Acta 47, p. 120–132, particularly p. 124 (1964). Tertiary phosphine sulfides may with particular advantage also be converted into the corresponding phosphine oxide by the process of European Offenlegungsschrift No. 170,101 corresponding to U.S. Pat. No. 4,675,446 or U.S. patent application Ser. No. 905,170 by means of $H_2O_2$. The process of U.S. Pat. No. 4,675,446 is carried out in a solvent comprising to at least about 20% by weight, lower aliphatic carboxylic acids and/or anhydrides thereof (remainder: other inert solvents); in the process of the second patent application, a solvent is used which comprises to about 2 to 20% by weight —optionally halogenated—13 ower aliphatic carboxylic acids and the remainder mono- and/or polyhydric aliphatic or cycloaliphatic alcohols—if appropriate as a mixture with other inert solvents which are miscible with the carboxylic acid/alcohol mixture.

The indirect route to the corresponding phosphine oxides via the tertiary aromatic phosphine sulfides is necessary here since the Friedel-Craft reaction of $POCl_3$ with benzene and haloaromatics does not succeed or at least hardly succeeds.

The known processes for the preparation of bis(4-halophenyl)phenylphoshine sulfides are not satisfactory or not completely satisfactory in various respects, particularly in industrial respects. The abovementioned Grignard reaction, starting from dichlorophenylphosphine or phenylphosphinic dichloride and halophenylmagnesium halide, cannot be carried out very simply industrially.

The Friedel-Crafts reaction according to German Patent No. 1,238,024, starting from $PSCl_3$ and halobenzene, leads—according to Example 7 to 9—to maximum yields of only about 63% (Example 8), at least in the case where chlorobenzene is used as halobenzene, of an isomeric mixture—probably comprising approximately equal parts—of bis(4-chlorophenyl)- and bis(2-chlorophenyl)thiophosphinic chloride. The bis(4-chlorophenyl)thiophosphinic chloride is just the precursor for the bis(4-chlorophenyl)phenylphosphine sulfide which is desired for the polymers sector.

In attempting to find an improved process for the preparation of bis(4-halophenyl)phenylphosphine sulfides, it has already been proposed (European Offenlegungsschrift No. 170,102, corresponding to U.S. Pat. No. 4,670,601) that this task be solved by a further development of the process described in German Patent No. 1,238.024. This European Patent Application relates to a process for the preparation of tertiary aromatic phosphine sulfides of the formula

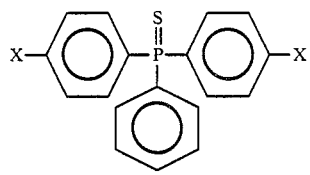

in which X=F, Cl or Br, by Friedel-Crafts reaction of P-Cl compounds with benzene and a halobenzene; the process comprises (a) heating phosphorus trichloride PCl₃ with an aluminum halide and benzene in the molar ratio 1:approximately 1 to 3:5:approximately 1 until the reaction is complete, and subsequently, without isolating the intermediate, again heating, after addition of an equimolar—compared to PCl₃—amount of elemental sulfur and approximately 2 to 10 times the molar amount of halobenzene of the formula C₆H₅X, in which X has the abovementioned meaning, if appropriate with further addition of aluminum halide (if a PCl₃:Al halide molar ratio of 1:approximately 2-3.5 has not already been employed at the beginning) to the completion of the reaction, and working up the reaction product as usual, or (b) heating phosphorus thiochloride PSCl₃, aluminum halide and a halobenzene of the formula C₆H₅X, in which X has the abovementioned meaning, in the molar ratio 1:approximately 1-3.5:2 until the reaction is complete, and subsequently, without isolating an intermediate, again heating, after addition of approximately 1 to 10 times the molar amount—compared to PSCl₃—of benzene, until the reaction is complete, and working up the reaction batch as usual.

Reactions (a) and (b) are based on the following reaction equations:

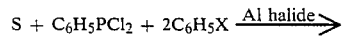

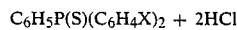

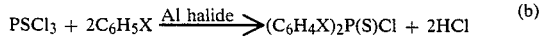

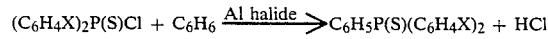

By this process (that is both by version (a) and by version (b)), the bis(4-halophenyl)-phenylphosphine sulfides, and only relatively few isomers and other byproducts, are obtained to a by far predominant extent—namely in yields consistently between about 65 and 75% of theory, relative to the starting PCl₃ or P(S)Cl₃—in a type of one-pot reaction (since no intermediate is isolated).

During further work on the process of European Offenlegungsschrift No. 170,102, corresponding to U.S. Pat. No. 4,670,601, it has now been found that substituted benzene may alternatively be employed in place of the unsubstituted benzene without disadvantage, admittedly not in version (a), but only in version (b).

The invention thus relates to a process for the preparation of tertiary aromatic phosphine sulfides of the formula I

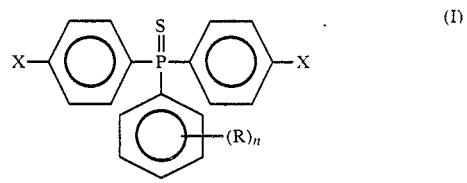

in which

X denotes F, Cl or Br,

R denotes a lower alkyl radical having 1 to 5 carbon atoms, aryl, aryloxy, and aralkyl, each suitably having a maximum of 2 aromatic nuclei, and n denotes an integer from 1 to 5, where the sum of the carbon atoms (R)ₙ is suitably a maximum of 12, and R denoting identical or different radicals when n is greater than 1.

The process comprises heating phosphorus thiochloride PSCl₃, an aluminum halide in which the halogen is preferably chlorine and/or bromine, and a halobenzene of the formula C₆H₅X in which X has the abovementioned meaning, in the molar ratio 1:(at least 1):(2 to 2.5), preferably 1:(1 to 3.5):(2 to 2.5), and subsequently, without isolating an intermediate, adding approximately 1 to 10 times the amount—relative to PSCl₃—of an aromatic of the formula II (see patent claim 1), in which R and n have the abovementioned meaning, and again heating until the reaction is complete, where further aluminum halide may be added before or during the heating, and working up the reaction batch in the usual fashion.

The reaction equations on which the reaction is based are:

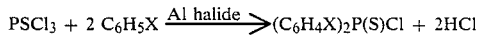

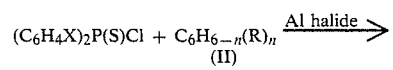

X, R and n have the abovementioned meaning.

The bis(4-halophenyl)arylphosphine sulfides, and only relatively few isomers and other byproducts, are obtained by this process in yields which are consistently between about 70 and 80% of theory, relative to the starting PSCl₃, in a type of one-pot reaction (since no intermediate is isolated).

This is very surprising since, according to Example 4 of German Patent No. 1,238,034 for example, an isomeric mixture of tristolylphosphine sulfide is obtained to a predominant extent by Friedel-Crafts reaction of PSCl₃ with toluene.

The success of the process according to the invention is also surprising since an unclear isomeric distribution in the final product and an unsatisfactory yield are obtained, as several experiments have shown, by version (a) of the process of European Offenlegungsschrift No. 170,102, corresponding to U.S. Pat. No. 4,670,601—with substituted aromatics of the formula II in place of the unsubstituted benzene.

The process according to the invention proceeds from $PSCl_3$ or an equimolar mixture of $PCl_3$ and elemental sulfur (which gives $PSCl_3$ in the presence of Al halide), Al halide and fluorobenzene, chlorobenzene or bromobenzene, usually in the molar ratio 1:(1 to 3.5):(2 to 2.5).

$AlCl_3$, $AlBr_3$ or alkylaluminum chloride or bromide are employed, for example, as aluminum halide; $AlCl_3$ is the particularly preferred aluminum halide.

Amongst the halobenzenes $C_6H_5X$ (X=F, Cl or Br), fluorobenzene and chlorobenzene are preferred.

A further excess of Al halide is possible, but not advantageous.

The reactants are mixed and heated until the reaction is complete. The reaction temperature is generally 70°–150° C. and should not exceed about 150° C. when chlorobenzene or bromobenzene are used and about 120° C. when fluorobenzene is used. The reaction time is generally about 1 to 10 hours. It is suitable to carry out the reaction under an inert gas atmosphere (nitrogen, argon, etc.).

When the first reaction step is complete, the mixture is suitably cooled and about 1 to 10 moles, preferably about 3 to 6 moles, relative to the starting $PSCl_3$, of an aromatic of the formula II, and, if appropriate, Al halide, are added.

The total amount of the Al halide employed (in both reaction steps) is preferably not significantly more than about 3.5 moles/mole of $PSCl_3$.

Of the $C_3$–$C_5$-alkyl radicals in the formula II, the branched radicals are particularly suitable. The aromatic radical is preferably mononuclear, i.e. the preferred aryl radical is the phenyl radical, the preferred aryloxy radical is the phenoxy radical and the preferred aralkyl radical is the benzyl radical.

All radicals R may, if appropriate, also be substituted by groups which are inert under the reaction conditions.

Particularly preferred aromatics of the formula II are the compounds (a) having $R=(C_2H_5$, particularly $CH_3$ and n=1 to 4, and (b) having $R=C_6H_5$ or $OC_6H_5$ and n=1.

Examples of aromatics of the formula II—that is both preferred and not preferred—are toluene, the various xylenes, trimethylbenzenes, tetramethylbenzenes, particularly 1,2,4,5-tetramethylbenzene, pentamethylbenzene, ethylbenzene, isopropylbenzene, diisopropylbenzene, tert.butylbenzene, di-tert.-butylbenzene, tri-tert.-butylbenzene, isoamylbenzene, diphenyl, terphenyl, quaterphenyl, triphenylbenzenes, diphenyl ether, and diphenylmethane. Although the reaction according to the invention succeeds using condensed aromatics (naphthalene, tetrahydronaphthalene, anthracene, phenanthrene, etc.) in place of those of the formula II, it is not quite so smooth.

The reaction mixture is again heated in the second step, preferably under reflux, until the reaction is complete. The reaction time here is normally between about 8 and 20 hours.

The completion of the individual part-reactions of the process according to the invention can be detected, for example, from the completion of the hydrogen chloride evolution (see the reaction equation) or by following the reaction progress in a conventional fashion (for example using chromatographic methods).

In both reaction steps, inert solents may also be employed—particularly for the purpose of regulating the reaction temperature when refluxing. Such inert solvents may be, for example, aliphatic hydrocarbons, such as petroleum ether, hexane, octane; cycloaliphatic hydrocarbons, such as cyclohexane; hydroaromatics, such as decahydronaphthalene, etc.

The reaction products which are produced are worked up in principle by conventional methods. To this purpose, the resultant reaction mixtures are decomposed suitably, with cooling, using excess water or an aqueous mineral acid (for example hydrochloric acid). To achieve better phase separation, a suitable organic inert solvent may be added—if not already present—under certain circumstances, the abovementioned inert solvents also being suitable for this purpose. If solvent or excess halobenzene or benzene is to be separated off, the entire organic phase is subjected to a distillation after drying. The distillation residues which are produced during this essentially represent the desired bis(4-halophenyl)arylphoshine sulfides in crude form. They are purified in a conventional fashion, expediently by distillation or recrystallization. The thiophosphinic halides (which are derived from incomplete reactions), which may easily be separated off by distillation, can be re-used in repeat batches. The overall yield can thus be increased still further.

The bis(4-halophenyl)arylphosphine sulfides which can be obtained according to the invention can be used in the same fashion as the bis(4-halophenyl)phenylphosphine sulfides; the preferred use is the employment for the preparation of polymers (by reaction with certain bisphenols).

The bis(4-halophenyl)arylphosphine sulfides of the formula I having
X=F, Cl or Br,
R=($C_1$–$C_5$)-alkyl, phenyl, phenoxy and/or benzyl, and
n=1 to 5 are new.

Amongst these, the preferred compounds are those having
X=F or Cl, and
(a) $R=C_2H_5$ and, particularly, $CH_3$, and n=1 to 4, and also
(b) $R=C_6H_5$ or $OC_6H_5$ and n=1.

The following examples are intended to further describe the invention. A comparison example (B), which shows that versions (A) of the process of European Offenelgungsschrift No. 170,102, corresponding to U.S. Pat. No. 4,670,601—when a substituted benzene (toluene) is used in place of unsubstituted benzene—only produces a low yield of the desired isomer, follows the examples of the invention (A).

(A) Examples of the invention

1. Bis(3-fluorophenyl)(4-methylphenyl)phosphine sulfide and oxide

A mixture of 127 g (0.75 mol) of $PSCl_3$, 180 g (1.34 mol) of aluminum chloride, 166 g (1.66 mol) of fluorobenzene and 117 g of cyclohexane (solvent and diluent) are refluxed for 8 hours. The mixture is cooled, 276 g (3 mol) of toluene are added, and the mixture is again refluxed for 5 hours. After cooling, the mixture is poured into 650 g of water, with cooling, and the aqueous phase is separated off and again washed with water. Volatile components were stripped off under reduced pressure. 260 g of a clear oil remained which, according to $^1$H and $^{31}$P NMR spectroscopy, comprised the desired bis(4-fluorophenyl)-4-methylphenylphosphine sulfide to 85%.

For the purpose of further characterization, the crude product was converted into the phosphine oxide by the process of European Offenlegungsschrift No. 170,101. For this purpose, it was dissolved in 315 g of acetic acid and 475 g of methanol, and 90.4 g (0.93 mol) of 35% strength hydrogen peroxide were added dropwise under reflux conditions. The mixture was cooled, the sulfur was filtered off, and the mixture was evaporated under reduced pressure. The residue was stirred with 2N NaOH, and the warm organic phase was separated off and washed again with water. After bulb tube distillation at 225° C./0.1 mbar, 224 g of a clear distillate were obtained which slowly crystallized. According to $^1$H NMR, $^{31}$P NMR and GC analysis, the product comprised.

2.94% of tris(4-fluorophenyl)phosphine oxide,
87.22% of bis(4-fluorophenyl)(4-methylphenyl)phosphine oxide,
2.31% and
4.22% of two other bis(fluorophenyl)(methylphenyl)phosphine oxides
1.00% of 4-fluorophenylbis(4-methylphenyl)phosphine oxide and
2.31% of unknown substances.

An overall yield of 79.3% of the desired bis(4-fluorophenyl)(4-methylphenyl)phosphine oxide corresponded to this.

A recrystallized sample had the melting point 96°–98° C.

2.
Bis(4-Fluorophenyl)(2,3,5,6-tetramethylphenyl)phosphine sulfide

A mixture of 63.5 g (0.375 mol) of PSCl$_3$, 90.0 g (0.675 mol) of AlCl$_3$, 80.0 g (0.832 mol) of fluorobenzene and 58.0 g of cyclohexane (solvent and diluent) were refluxed for 8 hours. The mixture was cooled, 200 g (1.49 mol) of 1,2,4,5-tetramethylbenzene (Durol) and 40 g (0.30 mol) of AlCl$_3$ were added, and the mixture was refluxed for a further 6 hours. The solution obtained was added dropwise, with cooling, to a mixture of 650 g of water and 216 g of toluene (as diluent). The organic phase was separated off and washed with water, and volatile components were removed in a vacuum of 0.1 mbar up to a bottom temperature of 100° C. 130 g of a pale yellow, highly viscous residue, which, according to chromatographic and $^1$HNMR spectroscopic investigations, represented virtually exclusively bis(4-fluorophenyl)(2,3,5,6-tetramethylphenyl)phosphine sulfide, were obtained. A yield of 89.7%, relative to phosphorus thiochloride employed, corresponds to this.

For the purpose of further characterization, a sample was converted into the phosphine oxide under the conditions specified in Example 1. Distillation was omitted; in place of this, the sample was recrystallized from cyclohexane/toluene. Bis(4-fluorophenyl)(2,3,5,6-tetramethylphenyl)phosphine oxide was obtained as a white powder, melting point 171°–173° C.

(B) Comparison example

Bis(4-Fluorophenyl)(4-methylphenyl)phosphine oxide

The comparison example was carried out corresponding to Example 2=version (a) of the process of European Offenlegungsschrift No. 170,102, corresponding to U.S. Pat. No. 4,670,601, but using toluene in place of benzene. 13.73 g (0.1 mol) of phosphorus trichloride, 29.33 g (0.22 mol) of aluminum chloride and 9.21 g (0.1 mol) of toluene were warmed for 6 hours at 80° C. The mixture was cooled, 3.2 g (0.1 mol) of sulfur and 57.67 g (0.6 mol) of fluorobenzene were added, and the mixture was refluxed for a further 10 hours. The reaction mixture was poured onto ice and extracted with methylene chloride, and the organic phase was separated off. After washing with water, volatile components were stripped off on a rotary evaporator and the residue was distilled in a bulb tube. 21 g of a yellow oil, which was converted, for the purpose of better characterization, into the phosphine oxide by the process of European Offenlegungsschrift No. 170,101, corresponding to U.S. Pat. No. 4,675,446, were obtained. For this purpose, it was dissolved in 100 g of glacial acetic acid. 8.5 g (0.0875 mol) of 35% strength hydrogen peroxide were then slowly added dropwise at 60° C., and the mixture was stirred for 1 hour at 60° C. According to a thin layer chromatogram, phosphine sulfide could no longer be detected. The mixture was cooled, sulfur was filtered off, and the filtrate was evaporated. After dilution with methylene chloride, acidic impurities were washed out using 2N sodium hydroxide solution, the methylene chloride was removed by distillation under reduced pressure, and the residue was distilled in a bulb tube at 225° C./0.1 mbar. 17 g of a brown resin, which, according to a gas chromatogram, only comprised the desired bis(4-fluorophenyl)(4-methylphenyl)phosphine oxide to 34.19%, were obtained. An overall yield of 17.7% of theory, relative to phosphorus trichloride, corresponds to this. The residue comprised isomers and unidentified products.

We claim:

1. A compound of the formula I,

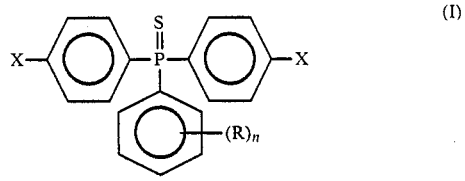

in which
X is F, Cl or Br,
R is alkyl having from 1 to 5 carbon atoms, aryl, aryloxy or aralkyl, each having at most 2 aromatic nuclei, and
n is an integer from 1 to 5,
a plurality of R representing equal or different of said substituents, (R)$_n$ having at most 12 carbon atoms and with the proviso that R is in p-position, if n is 1 and R is alkyl.

2. A compound according to claim 1, wherein any aromatic group contained in R is mononuclear.

3. A compound of the formula I,

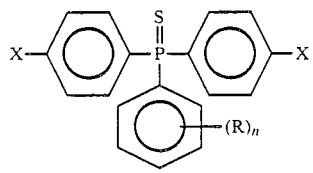

in which
X is F, Cl or Br,
R is CH₃ or C₂H₅, and
n is an integer from 1 to 4, with the proviso that R is in p-position, if n is 1.

4. A compound as claimed in claim 3, in which (R)ₙ is 2,3,5,6-tetramethyl.

5. A compound according to claim 1, wherein any C₃-C₅ alkyl group in R is branched.

6. A compound according to claim 3, in which X is F or Cl, R is C₂H₅ and n is an integer from 1 to 4.

7. A compound according to claim 3 in which X is F or Cl, R is CH₃ and n is an integer from 1 to 4.

8. A compound according to claim 2, wherein X is F or Cl, R is C₆H₅ and n is 1.

9. A compound according to claim 2, wherein X is F or Cl, R is OC₆H₅ and n is 1.

10. A process for the preparation for the production of tertiary aromatic phosphane sulfides of the formula I

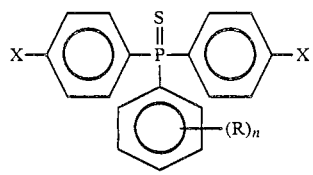

in which
X is F, Cl or Br,
R is alkyl having from 1 to 5 carbon atoms, aryl, aryloxy or aralkyl, each having at most 2 aromatic nuclei, and
n is an integer from 1 to 5,
a plurality of R representing equal or different of said substituents, (R)ₙ having at most 12 carbon atoms and with the proviso that R is in p-position, if n is 1 and R is alkyl, which comprises heating phosphorus thiochloride PSCl₃, an aluminum halide and a halobenzene of the formula C₆H₅X in which X has the meaning indicated here-before, in a molar ratio of 1:(at least 1):(2 to 2.5) and adding subsequently and without isolating an inter-mediate product an aromatic compound of the formula II

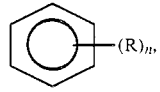

in an amount in the range from the equal to the 10 fold molar amount of PSCl₃, in which compound of formula II R and n have the meaning indicated above, and again heating the mixture to complete the reaction with or without addition of further aluminum halide, and subsequently recovering the compound of formula I.

11. A process according to claim 10, wherein the aluminum halide is aluminum bromide or aluminum chloride AlCl₃.

12. A process according to claim 10, wherein the molar ratio of the aluminum halide to PSCl₃ is in the range from 1 to 3.5.

13. A process according to claim 10, wherein the halobenzene C₆H₅X used is fluoro- or chlorobenzene.

14. A process according to claim 10, wherein the reaction is carried out at a temperature in the range from 70° to 150° C.

15. A process according to claim 14, wherein the compound of the formula C₆H₅X is fluorobenzene and the reaction temperature does not exceed 120° C.

16. A process according to claim 10, wherein after the first reaction stage, the reaction mixture is cooled and wherein subsequently 1 to 10 moles, calculated on the amount of PSCl₃ used as starting material are added thereto, and also the aromatic compound of the formula II, and the reaction mixture is then again heated until completion of the reaction with or without the addition of further aluminum halide.

17. A process according to claim 10, wherein after the first reaction stage, the reaction mixture is cooled and wherein subsequently 3 to 6 moles, calculated on the amount of PSCl₃ used as starting material are added thereto, and also the aromatic compound of the formula II, and the reaction mixture is then again heated until completion of the reaction with or without the addition of further aluminum halide.

18. A process according to claim 10, wherein the reaction is carried out under an atmosphere of an inert gas.

* * * * *

UNITED STATES PATENT AND TRADEMARK OFFICE
CERTIFICATE OF CORRECTION

PATENT NO. : 4,847,419

DATED : July 11, 1989

INVENTOR(S) : Weiss, et al.

It is certified that error appears in the above-identified patent and that said Letters Patent is hereby corrected as shown below:

Col. 2, line 10, insert -- 2MgBrCl -- after " 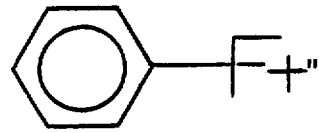 to complete the first reaction equation.

Col. 2, line 17, delete "2MgBrCl".

Col. 4, line 46, "halogenated—13 ower" should read -- halogenated—lower -- .

Col. 8, line 7, "solents" should read -- solvents -- .

Col. 11, line 15, claim 4 is dependent upon <u>claim 7</u> and not claim 3.

UNITED STATES PATENT AND TRADEMARK OFFICE
CERTIFICATE OF CORRECTION

PATENT NO. : 4,847,419

DATED : July 11, 1989

INVENTOR(S) : Weiss, et al

It is certified that error appears in the above-identified patent and that said Letters Patent is hereby corrected as shown below:

Col. 11, line 27, in claim 10 delete "for the preparation".

Signed and Sealed this

Twenty-sixth Day of February, 1991

*Attest:*

HARRY F. MANBECK, JR.

*Attesting Officer*      *Commissioner of Patents and Trademarks*